United States Patent [19]
Carlson et al.

[11] Patent Number: 5,827,319
[45] Date of Patent: Oct. 27, 1998

[54] RADIALLY EXPANDABLE ACCESS SYSTEM HAVING DISPOSABLE AND REUSABLE COMPONENTS

[75] Inventors: John E. Carlson, Mountain View; Robert K. Deckman, San Mateo; Steven P. Masterson, San Francisco; Thomas J. Palermo, San Jose; Craig K. Tsuji, Santa Clara, all of Calif.

[73] Assignee: Innerdyne, Inc., Sunnyvale, Calif.

[21] Appl. No.: 650,387

[22] Filed: May 20, 1996

[51] Int. Cl.⁶ .................................................. A61M 29/00
[52] U.S. Cl. ........................... 606/191; 604/264; 606/185
[58] Field of Search ....................... 604/52, 53, 104–109, 604/164, 166, 171, 172, 264, 280; 606/191, 108, 198; 600/201

[56] References Cited

U.S. PATENT DOCUMENTS

| | | | |
|---|---|---|---|
| 3,788,318 | 1/1974 | Kim et al. | 604/164 |
| 3,789,852 | 2/1974 | Kim et al. | 604/164 |
| 5,183,464 | 2/1993 | Dubrul et al. | |
| 5,431,676 | 7/1995 | Dubrul et al. | |

FOREIGN PATENT DOCUMENTS

| | | |
|---|---|---|
| 0515867 | 12/1992 | European Pat. Off. . |
| 2625429 | 7/1989 | France . |
| WO9307819 | 4/1993 | WIPO . |
| WO 94/20026 | 9/1994 | WIPO . |
| WO9515724 | 6/1995 | WIPO . |

*Primary Examiner*—William Lewis
*Attorney, Agent, or Firm*—Townsend and Townsend and Crew LLP

[57] ABSTRACT

An access system comprises a radially expandable sleeve, a pneumoperitoneum needle, a cannula assembly, and an obturator. Methods for reconstructing and reusing the access system comprise replacing the radially expandable sleeve and cannula valve cap components of the system, both of which are disposable. All remaining system components may be sterilized and reused one or more times. The pneumoperitoneum needle can be separated into tubular needle body and needle stylet components, which may be separately replaced or sterilized and reused. Similarly the cannula comprises both a cannula hub and a cannula tube, where the hub and tube may be separately replaced or sterilized.

19 Claims, 7 Drawing Sheets

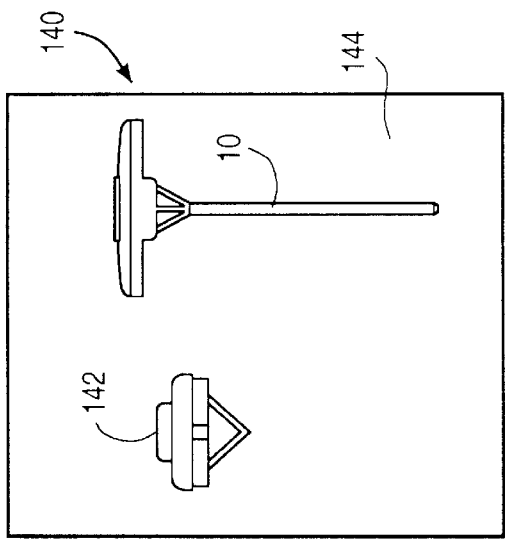
FIG. 9
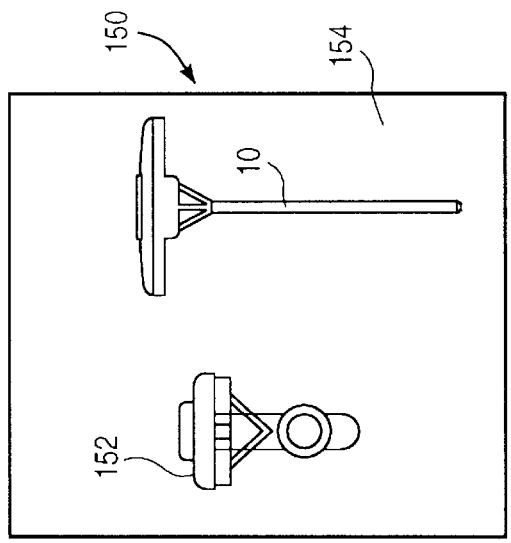
FIG. 10
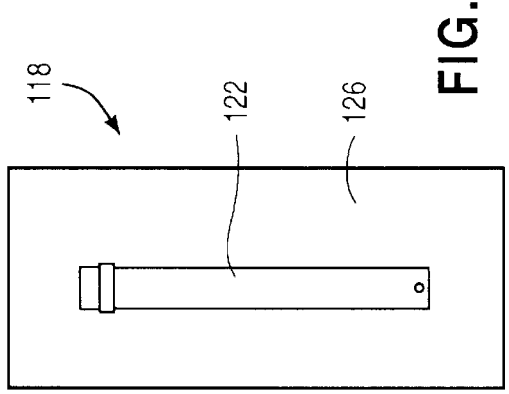
FIG. 11
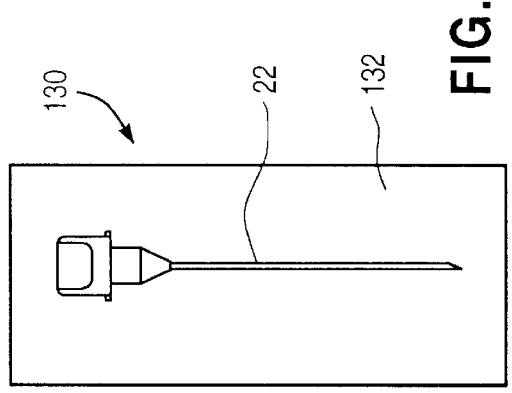
FIG. 12
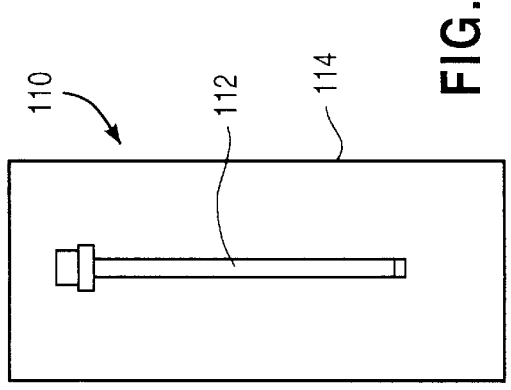
FIG. 13
FIG. 14

5,827,319

RADIALLY EXPANDABLE ACCESS SYSTEM HAVING DISPOSABLE AND REUSABLE COMPONENTS

BACKGROUND OF THE INVENTION

1. Field of the Invention

The present invention relates generally to apparatus and methods for providing access to an internal operative site during a surgical procedure. More particularly, the present invention relates to an access system which can be percutaneously or otherwise introduced while in a narrow diameter configuration and which after introduction can be radially expanded to accommodate passage of larger diameter surgical instruments.

Minimally invasive surgical procedures rely on obtaining percutaneous access to an internal surgical site using small-diameter access tubes (typically 5 to 12 mm), usually referred to as trocars, which penetrate through the skin and which open to the desired surgical site. A viewing scope is introduced through one such trocar, and the surgeon operates using instruments introduced through other appropriately placed trocars while viewing the operative site on a video monitor connected to the viewing scope. The surgeon is thus able to perform a wide variety of surgical procedures requiring only several 5 to 12 mm punctures at the surgical site. Patient trauma and recovery time are thus greatly reduced.

Particular minimally invasive surgical procedures are often referred to based on the type of scope used to view the region of the body which is the operative site. Thus, procedures in the abdominal area, which rely on a laparoscope for viewing, are referred to as laparoscopic procedures. In such laparoscopic procedures, the patient's abdominal region is typically insufflated (filled with pressurized gas) to raise the abdominal wall and create sufficient operating space to perform a desired procedure. The trocars used in laparoscopic procedures must therefore include a valve at their proximal end to allow passage of the scope or surgical instruments while inhibiting leakage of the insufflating gas. It has also been proposed to perform laparoscopic procedures by mechanically expanding the abdomen rather than using insufflation.

Other minimally invasive surgical procedures include thoracoscopic procedures performed in the region of the chest, arthroscopic procedures performed in body joints, particularly the knee, gynecological laparoscopic procedures, and endoscopic surgical procedures performed in various regions of the body, typically with a flexible scope. These latter procedures do not always employ pressurization and the trocars used may not include pressure valves at their proximal ends.

Recently, a radially expandable access system has become commercially available under the trademark STEP™ from InnerDyne Medical, Sunnyvale, Calif., assignee of the present application. Certain aspects of the STEP™ access system are described in U.S. Pat. Nos. 5,183,464 and 5,431,676, which are assigned to the assignee of the present application. The STEP™ access system includes a pneumoperitoneum needle, an expandable sleeve component which is percutaneously introduced while positioned over the pneumoperitoneum needle, a cannula having a pneumostasis valve permanently affixed at its proximal end, and an obturator which is removably inserted into the cannula to form an expansion member for the sleeve. After the needle/sleeve assembly has been percutaneously introduced, and the peritoneal cavity insufflated in the case of laparoscopic procedures, the needle is removed from the sleeve, and the cannula/obturator assembly introduced through the sleeve. The sleeve, which initially has a diameter in the range of 2–3 mm, is thus expanded to a final diameter depending on the cannula size, which can be selected from 5 mm, 10 mm, or 12 mm. Use of the STEP™ access system has many advantages, including reduced trauma to the patient and the ability to replace a cannula with a larger diameter cannula through a previously introduced sleeve.

While the STEP™ access system represents a substantial advance over conventional trocars, the large number of components required to assemble all configurations of the system can present inventory problems for hospitals and other users. Moreover, it may be desirable to further increase the number of components in order to reduce the "disposable" content of the system, thus reducing costs associated with using the system.

For these reasons, it would be desirable to provide improved radially expandable access systems, component kits for such systems, and methods for reconstructing and reusing such systems. In particular, it would be desirable if the improved systems, kits, and methods would facilitate stocking and inventory management of the access systems. It would be further desirable if such improved systems, kits, and methods could help reduce costs associated with increasing the reusable content of the access systems.

2. Description of the Background Art

U.S. Pat. Nos. 5,183,464 and 5,431,676, have been described above. WO 94/20026, published on Sep. 15, 1994, corresponds to U.S. Pat. No. 5,431,676. The STEP™ access system is described in a package insert published by Inner-Dyne Medical, Sunnyvale, Calif.

SUMMARY OF THE INVENTION

According to the present invention, systems, kits, and methods are provided to improve the reusability and inventory maintenance of multiple-component radially expandable access systems of the type described above. In particular, the access systems are configured to increase the content of reusable components, thereby decreasing the content of disposable components, and thus reducing the cost of system use. Methods and kits for reconstruction and reuse of the access systems are also improved to be compatible with and take advantage of the new access system configuration.

The access system of the present invention comprises a radially expandable sleeve having an axial lumen therethrough. The system further includes a cannula comprising a cannula tube having a proximal end, a distal end, and a lumen therethrough. A cannula hub is fixedly attached to the proximal end of the cannula tube, and a valve cap having a pneumostasis valve therein is removably attached to the cannula hub. An obturator having a tapered distal end is removably received in the lumen of the cannula, and the cannula and obturator together form an expansion assembly which can be introduced through the radially expandable sleeve. The access system preferably further includes a pneumoperitoneum needle, which is initially placed within the lumen of the radially expandable sleeve to permit percutaneous introduction of the sleeve. The pneumoperitoneum needle preferably comprises an assembly of a tubular needle and an internal stylet which is removably received in the tubular needle. Usually, at least the valve cap will be disposable after each use. After an initial expansion, the sleeve material is generally unsuitable for reuse in another patient. Typically, both the valve cap and the radially expandable sleeve will be disposable after each use. Other components such as the tubular needle of the pneumoperitoneum needle will usually have a limited reuse, typically from 5 times to 30 times, while the remaining components will be reusable for a larger number of times, typically more than 100 times. Of course, any component which becomes damaged or excessively worn will be disposed of and replaced.

Methods according to the present invention for reusing the access system will comprise replacing at least the radially expandable sleeve, and usually both the sleeve and the valve cap, and sterilizing or replacing all other components of the system. In some cases, the cannula hub will be sterilized and the cannula tube replaced, while in other cases the entire cannula assembly will be sterilized and reused. In some cases, the tubular needle will be replaced and the stylet sterilized, while in other cases both the tubular needle and stylet will be sterilized and reused.

The method will further comprise reconstructing an expansion assembly by attaching a replacement valve cap onto the sterilized cannula tube and hub and inserting the sterilized obturator therethrough. Alternatively, the expansion assembly is reconstructed by attaching the replacement valve cap onto the sterilized cannula hub, attaching the replacement cannula tube to the cannula hub, and inserting the sterilized obturator through the cannula tube and hub.

The method preferably further comprises reconstructing a dilation assembly by inserting a sterilized or partly sterilized pneumoperitoneum needle into a central lumen of the replaced radially expandable sleeve. Both the tubular needle component and the stylet component of the pneumoperitoneum needle may have been sterilized prior to insertion into the radially expandable sleeve. Alternatively, at least one of the needle and stylet may have been replaced with the other component having been sterilized prior to inserting the needle into the radially expandable sleeve.

The present invention further provides kits for use in reconstructing the access system of the present invention. In a first instance, the kit comprises the radially expandable sleeve present in a package enclosing the sleeve. Usually, the package will further include the valve cap. In a second instance, the kit will comprise the valve cap by itself present in a package. In a third instance, the kit will comprise the cannula tube and hub present in a package. Such package may further comprise the obturator disposed in the same package. In a fourth instance, the kit comprises the obturator by itself present in a package. In a fifth instance, the kit comprises the cannula body present in a package. In a sixth instance, the kit comprises a tubular needle component of the pneumoperitoneum needle present in a package. The package may further comprise the stylet of the pneumoperitoneum needle in the same package. The package may be sterile or non-sterile, usually being sterile for the disposable components (the sleeve and usually the valve cap), and may comprise a pouch, box, tray, foam insert, envelope, or other conventional packing material of a type employed for medical instruments.

BRIEF DESCRIPTION OF THE DRAWINGS

FIG. 9 is a kit comprising a 5 mm cannula tube present in a package.

FIG. 10 illustrates a 10 mm cannula tube present in a package.

FIG. 11 illustrates a 12 mm cannula tube present in a package.

FIG. 12 illustrates the tubular needle component of a pneumoperitoneum needle assembly present in a package.

FIG. 13 illustrates a kit including the radially expandable sleeve and the valve cap of the access system of the present invention present in a package.

FIG. 14 illustrates a kit similar to that in FIG. 13, except that the valve cap is sized for 10 mm and 12 mm cannulas.

DESCRIPTION OF THE SPECIFIC EMBODIMENTS

The access system of the present invention is useful for forming and enlarging percutaneous penetrations into a variety of target locations within a patient's body for a multiplicity of purposes. Such purposes include drainage, intra-organ drug administration, feeding, perfusion, aspiration, and the like, most usually being the introduction of viewing scopes and surgical instruments for use in minimally invasive surgical procedures, such as laparoscopic procedures, thoracoscopic procedures, arthroscopic procedures, endoscopic procedures, and the like. In addition to percutaneous procedures, the access system of the present invention will find use in hysteroscopic, colonoscopic, and other procedures where access is established through existing body orifices.

The access systems of the present invention are particularly valuable in percutaneous procedures since they will create a very small initial penetration, usually being below about 5 mm, more usually being below about 4 mm, frequently being below about 3.5 mm, and preferably being 3 mm or below. The penetration will be subsequently enlarged to a desired final size, usually having a final diameter in the range from about 5 mm to 15 mm, more usually being from about 5 mm to 12 mm, and typically being from about 5 mm to 10 mm. The enlarged penetration will define an access lumen from the outside of the patient's body to the desired internal location, and it is a particular advantage of the present invention that the diameter of the access lumen can be changed as will be described in more detail hereinafter. In non-percutaneous procedures, the access system is valuable since it can pass through the existing body orifice in its narrow-diameter configuration and be subsequently expanded with minimum discomfort and trauma to the patient.

The access system of the present invention comprises a number of individual components that can be assembled into different size configurations. The assembled components can also be disassembled after use, and the components selectively sterilized or replaced prior to reassembling the access system for further use with a different patient. The different components and component assemblies and sub-assemblies will be described in greater detail below.

Sterilization of the components of the trocar system can be accomplished by any suitable conventional sterilization technique, including heat, e.g., steam and autoclaving; chemical treatment, e.g., ethylene oxide exposure; radiation, and the like. After use, reusable components will be washed to remove blood and other contaminating substances and then sterilized, preferably by exposure to steam. Disposable components will usually be radiation sterilized in their packages prior to distribution. Thus, disposable components will usually be ready to use out of the package.

Figure 1:
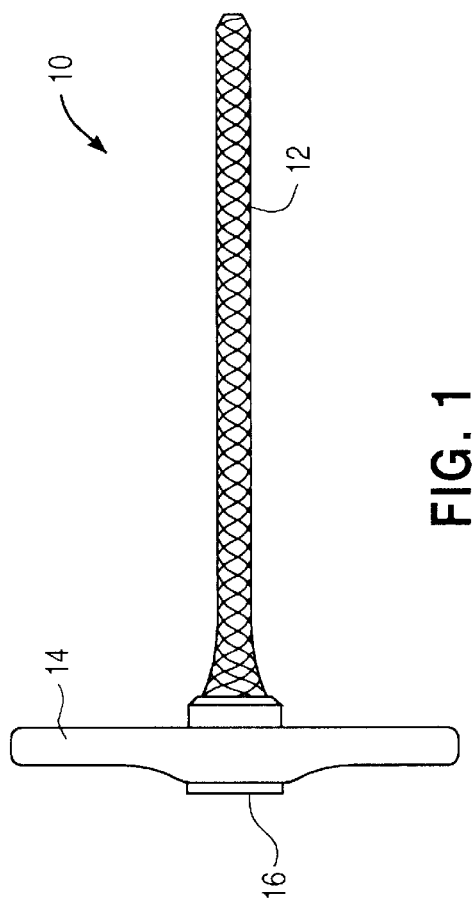
FIG. 1 is a side view of the radially expandable sleeve component of the access system of the present invention.

Referring now to FIG. 1, a first component of the access system of the present invention comprises radially expandable sleeve 10. The sleeve 10 includes a sleeve body, typically comprising a radially expandable braid covered by an elastomeric layer, e.g., polyurethane. The braid initially has an inner diameter of about 2 mm and an outer diameter of about 3.5 mm. As described in detail below, passage of an expansion assembly therethrough causes radial expansion of the sleeve, typically to a final diameter of 5 mm, 10 mm, or 12 mm. The sleeve 10 further comprises a handle at its proximal end. The handle includes a passage 16 therethrough, typically including a female bayonet connector coaxially located about the passage. The radially expandable sleeve 10 may be constructed in accordance with the details set forth in U.S. Pat. No. 5,431,676, the full disclosure of which is incorporated herein by reference.

Figure 2:
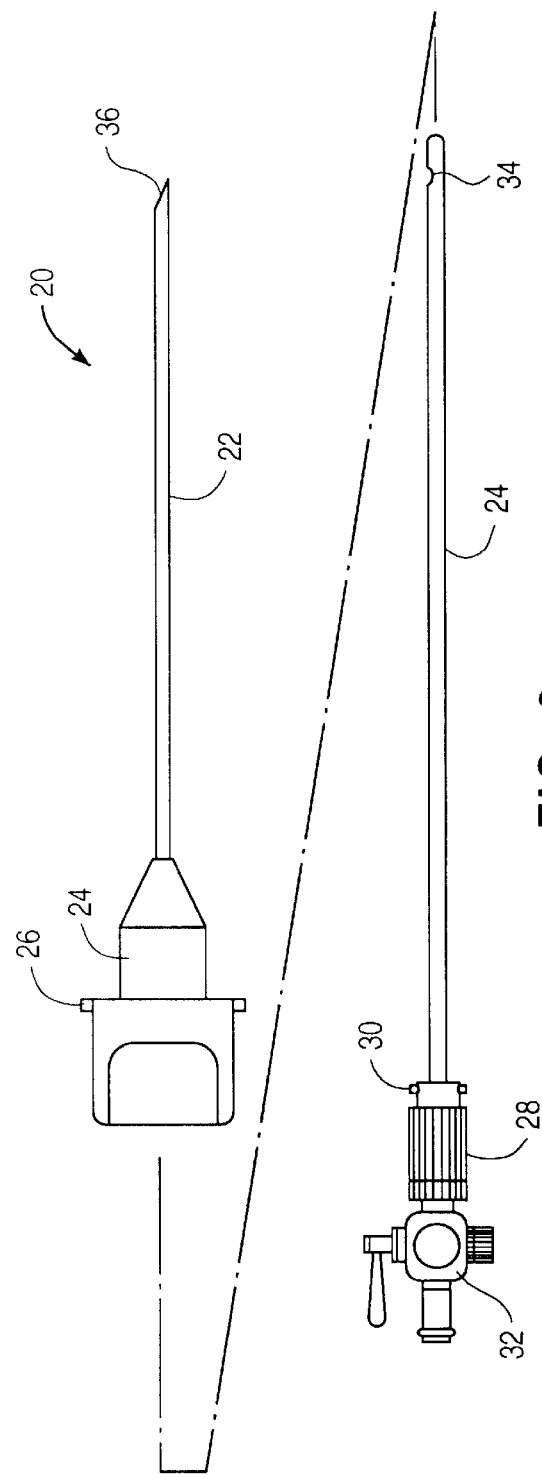
FIG. 2 is a side view of the pneumoperitoneum needle component of the access system of the present invention, shown with the stylet removed from the tubular needle body.

A pneumoperitoneum needle assembly 20 comprising a tubular needle body 22 and a stylet 24 is illustrated in FIG. 2. The tubular needle body 22 includes a hub 24 having a male bayonet connector 26 at a proximal end thereof. Stylet 24 is spring-loaded in a proximal connector 28 which comprises a male bayonet fitting 30 which is receivably mounted in a female bayonet fitting (not illustrated) in the hub 24. An insufflation valve 32 is connected to the proximal end of the stylet 24 and a port 34 is disposed in the distal end of the stylet, permitting insufflation gas introduced through the valve 32 to be released through the port 34. In use, the stylet 24 will be mounted within the tubular needle body 22 with the bayonet connector 30 attached to the hub 24. The distal end of the stylet will extend from distal end 36 of the needle, and the stylet will retract into the needle body 22 when the needle is engaged against tissue, as described in more detail below.

Figure 3:
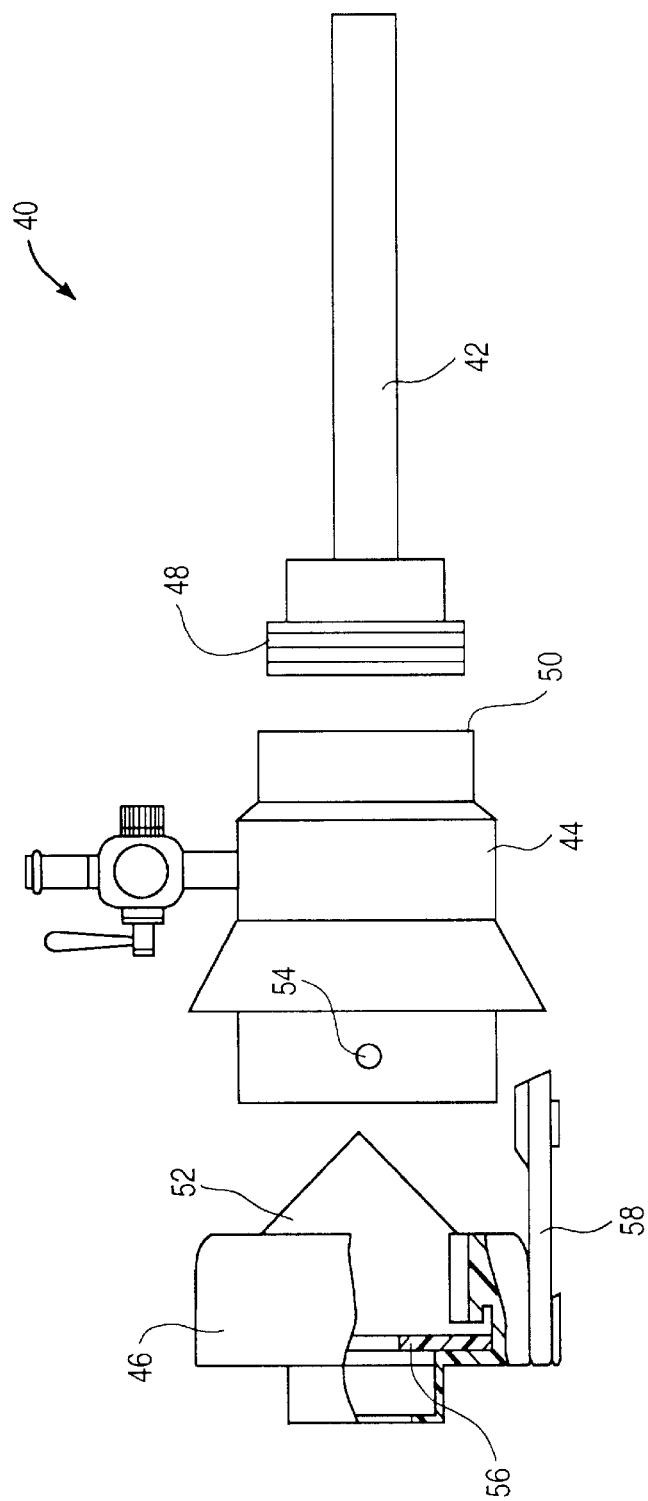
FIG. 3 is a side view of the cannula assembly of the access system of the present invention, shown with the cannula body, cannula hub, and valve cap, removed from each other, and further shown with the valve cap in partial section.

A cannula assembly 40 constructed in accordance with the principles of the present invention is illustrated in FIG. 3. Cannula assembly 40 comprises a cannula tube 42, a proximal hub 44, and a removable valve cap 46. The cannula tube 42 includes a threaded connector 48 at its proximal end which can be removably secured to a fitting 50 in the distal end of the cannula hub 44. The valve cap 46 includes a pneumostasis valve element 52 and mates with a male bayonet fitting 54 at the proximal end of the cannula hub 44.

A second disk valve element 56 is mounted in tandem with the pneumostasis valve element 52 to engage against a surgical instrument (not shown) when introduced through the cannula assembly 40. The valve element 56 is generally sized for a large instrument, e.g., 12 mm in diameter. A reducing element 58 is provided for reducing the port size of valve element 56 to accommodate smaller instruments, e.g., 10 mm.

Figure 4:
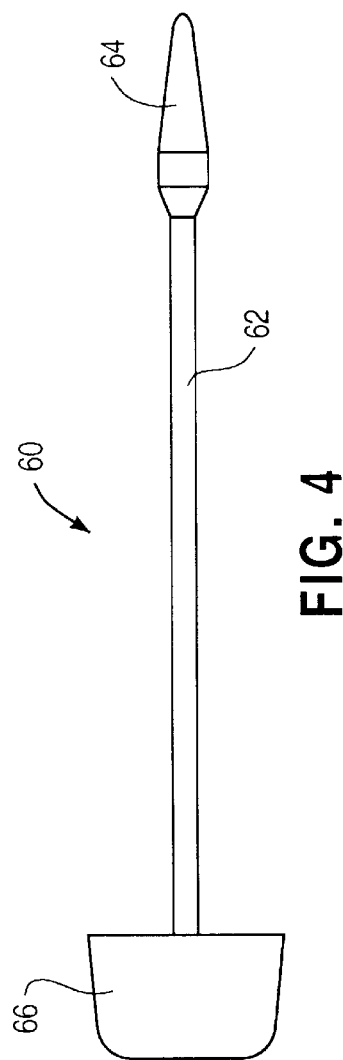
FIG. 4 is a side view of the obturator component of the access system of the present invention.

An obturator 60 comprising a shaft 62, tapered distal end 64, and handle 66 is illustrated in FIG. 4. The obturator 60 is intended to be placed within a central lumen of the cannula assembly 40 in order to form an expansion assembly for use as described below.

The access system components just described will generally differ in both size and reusability, with exemplary sizes and extent of reusability for each of the components set forth below in Table 1. Note that the radially expandable sleeve, pneumoperitoneum needle (including both the tubular needle body and the needle stylet), and the cannula hub will preferably come in just one size which is compatible with each of the three exemplary system sizes. It will be appreciated, of course, that the radially expandable sleeve is intended to conform to cannula tubes having each of the three sizes. The cannula hub will be sized sufficiently large to be compatible with each of the three sizes, and the valve cap will come in two sizes, with the larger size accommodating both 10 and 12 mm instruments, as described above. The cannula tube and obturator, in contrast, will be provided in each of the three system sizes.

TABLE 1

ACCESS SYSTEM COMPONENTS

| Component | Size(s) | Reusability |
| --- | --- | --- |
| Radially Expandable Sleeve | One | Disposable |
| Tubular Needle Body | One | Limited reuse |
| Needle Stylet | One | Unlimited reuse |
| Cannula Tube | 5 mm, 10 mm, 12 mm | Limited reuse |
| Cannula Hub | One | Unlimited reuse |
| Valve cap | 5 mm, 10/12 mm | Disposable or limited reuse |
| Obturator | 5 mm, 10 mm, 12 mm | Unlimited reuse |

Referring now to FIGS. 5–17, exemplary packages or "kits" containing various combinations of system components are illustrated. Providing such kits is a particularly convenient way to facilitate inventory maintenance of the components necessary to reconstruct the access systems of the present invention. It will be appreciated, of course, that complete systems could be sold in kits, as well as each of the individual components can be sold in kits. In many cases, it will be desirable to combine pairs of components or multiple pieces of a single component together in one package, particularly where the components are sized to match each other. The kits will include conventional package elements, typically pouches, envelopes, trays, boxes, foam inserts and other containers of a type commonly used for sterile or non-sterile packing of surgical instruments. The packages will typically also include a "package insert" which is a written instruction sheet with instructions on use, warnings, etc.

Figure 5:
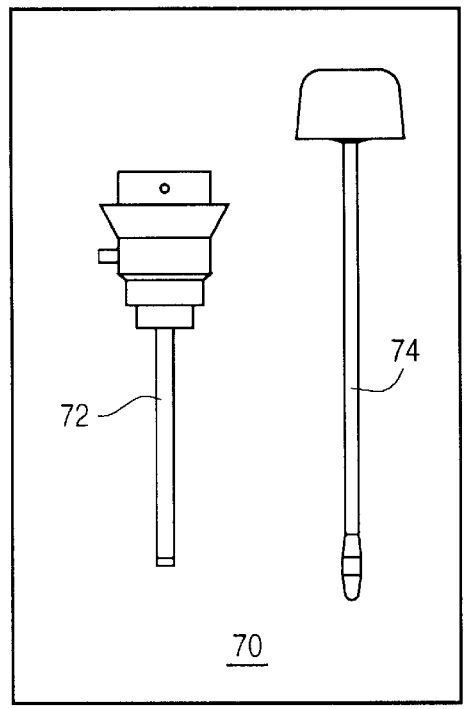
FIG. 5 illustrates a kit including a partial cannula assembly and an obturator present in a package, where the obturator and cannula are sized for a 5 mm trocar system.
Figure 8:
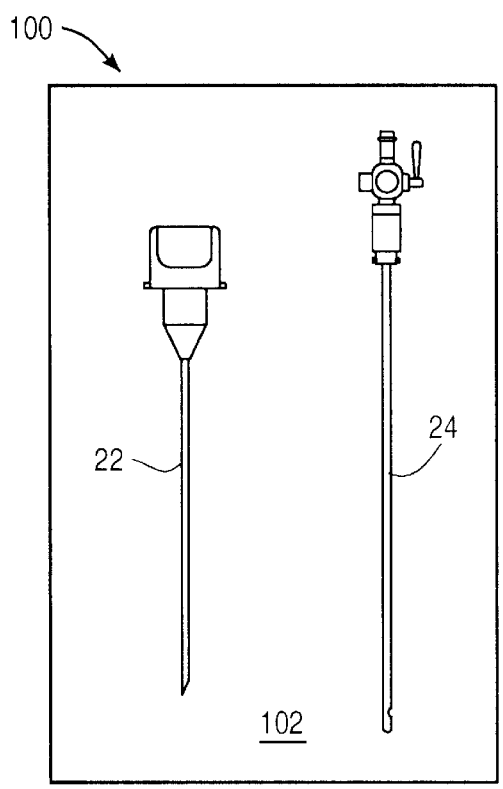
FIG. 8 is a kit comprising the tubular needle component and stylet of the pneumoperitoneum needle present in a package.

Referring now to FIG. 5, the kit 70 comprises a package, typically non-sterile since the reusable components can be subsequently sterilized, including a 5 mm cannula assembly 72 and a 5 mm obturator 74. The cannula assembly 72 includes both the cannula hub and the removable cannula tube, as described previously.

Figure 7:
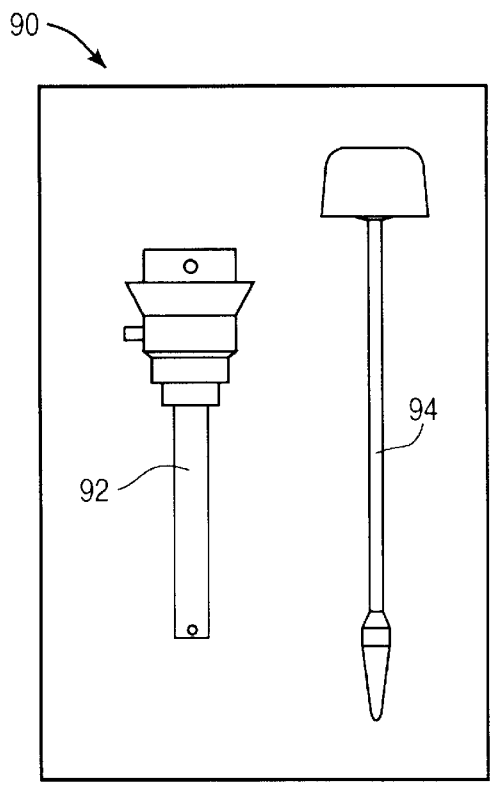
FIG. 7 is similar to FIGS. 5 and 6, except that the cannula and obturator are sized for a 12 mm access system.
Figure 6:
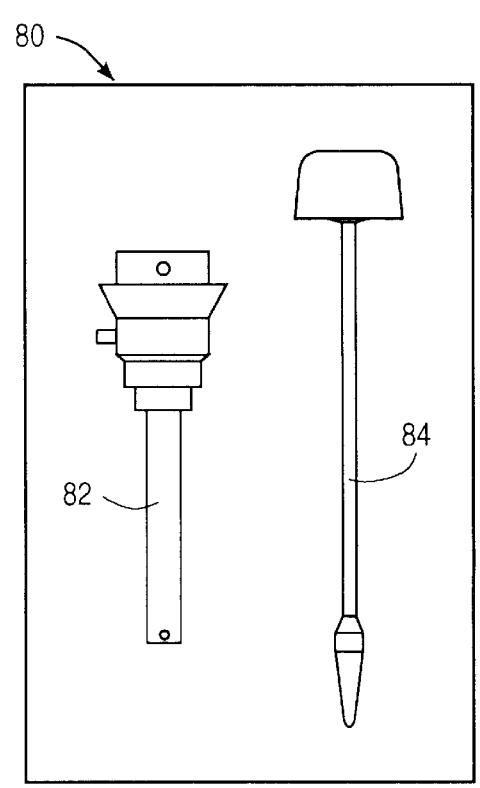
FIG. 6 is similar to FIG. 5, except that the obturator and cannula are sized for a 10 mm access system.

A second exemplary kit 80 including a 10 mm cannula assembly 82 and 10 mm obturator 84 is illustrated in FIG. 6. A similar kit 90 including a 12 mm cannula assembly 92 and 12 mm obturator 94 is illustrated in FIG. 7.

A kit 100 including both the tubular needle body 22 and stylet 24, as illustrated above, as illustrated in FIG. 8. The package 102 of the kit may be sterile or non-sterile.

Kits comprising individual components may also be provided. For example, a kit 110 including a 5 mm cannula body 112 in a sterile pack 114 is illustrated in FIG. 9. Similar kits 116 and 118 comprising a 10 mm cannula body 120 and a 12 mm cannula body 122 in sterile packs 124 and 126, respectively, are illustrated in FIGS. 10 and 11. A kit 130 comprising a tubular needle body 22, a sterile package 132 is illustrated in FIG. 12.

Figure 15:
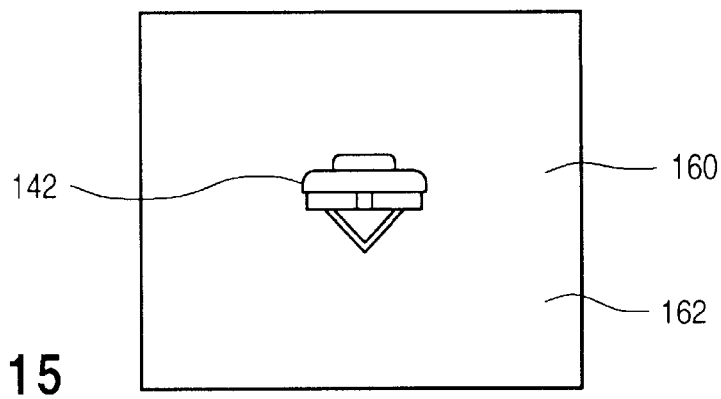
FIG. 15 illustrates a kit including a 5 mm valve cap assembly present in a package.
Figure 16:
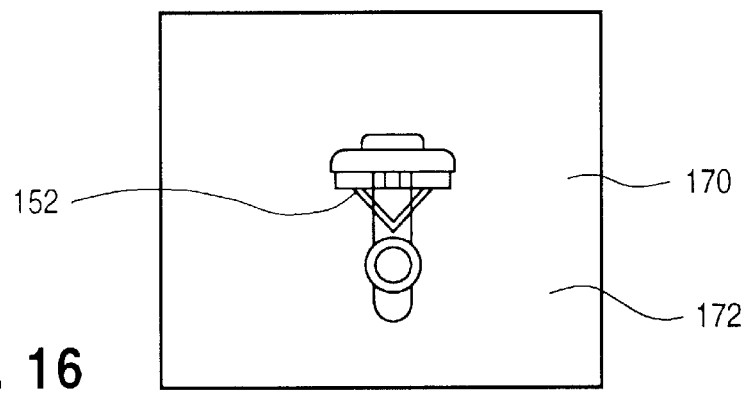
FIG. 16 illustrates a 10 mm/12 mm valve cap present in a package.
Figure 17:
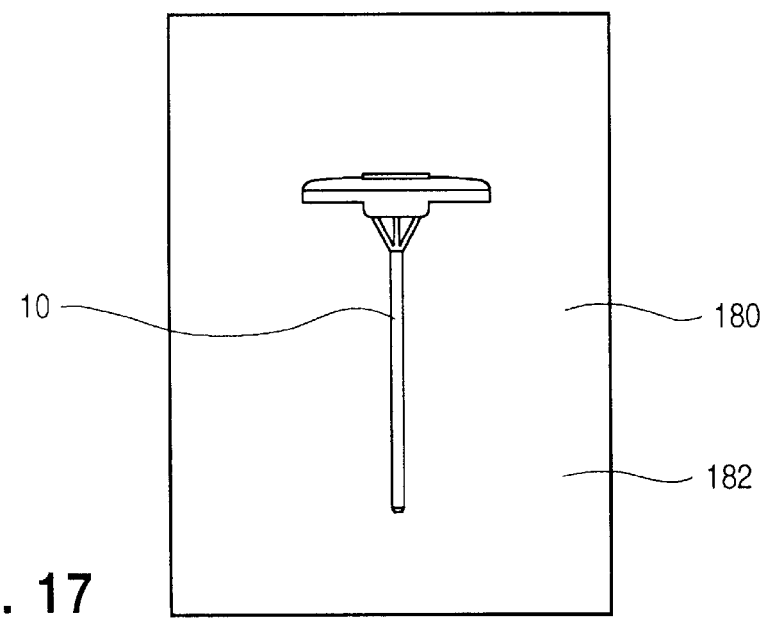
FIG. 17 illustrates a radially expandable sleeve present in a package.
Figure 18:
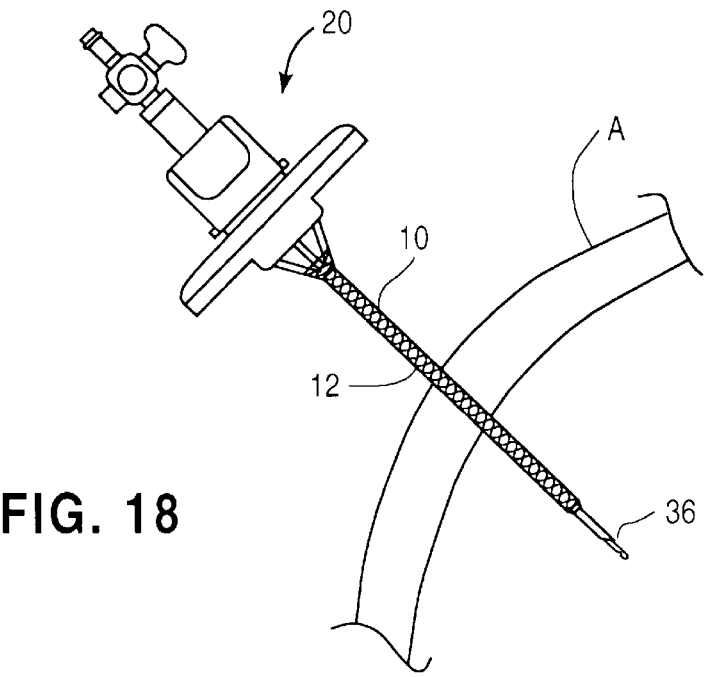
FIGS. 18–21 illustrate use of the access system of the present invention in providing access to a patient's abdomen.
Figure 19:
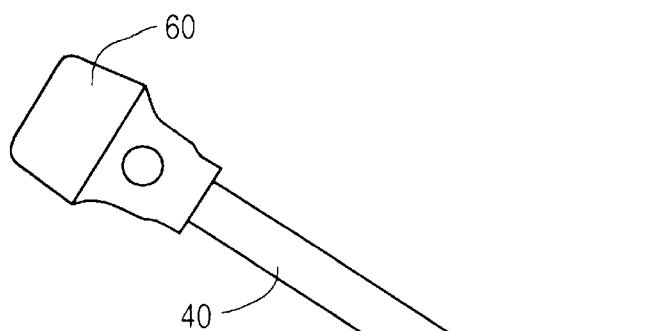
Figure 19:
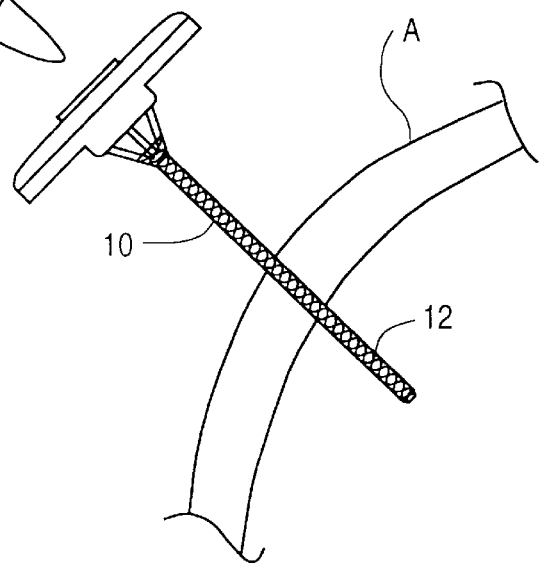

Kits comprising disposable components are illustrated in FIGS. 13–17. A kit 140 comprising a radially expandable sleeve 10 and a 5 mm valve cap 142 in a sterile package 144 is illustrated in FIG. 13. A similar kit 150 comprising a radially expandable sleeve 10 and a 10/12 mm valve cap 152 present in a sterile pack 154 is illustrated in FIG. 14. A kit 160 comprising one or more 5 mm valve caps 142 in a sterile package 162 is illustrated in FIG. 15. A kit 170 comprising one or more sterile 10/12 mm valve caps 152 in a sterile package 172 is illustrated in FIG. 16. Finally, a kit 180 comprising one or more radially expandable sleeves 10 in a sterile package 182 is illustrated in FIG. 17.

Figure 20:
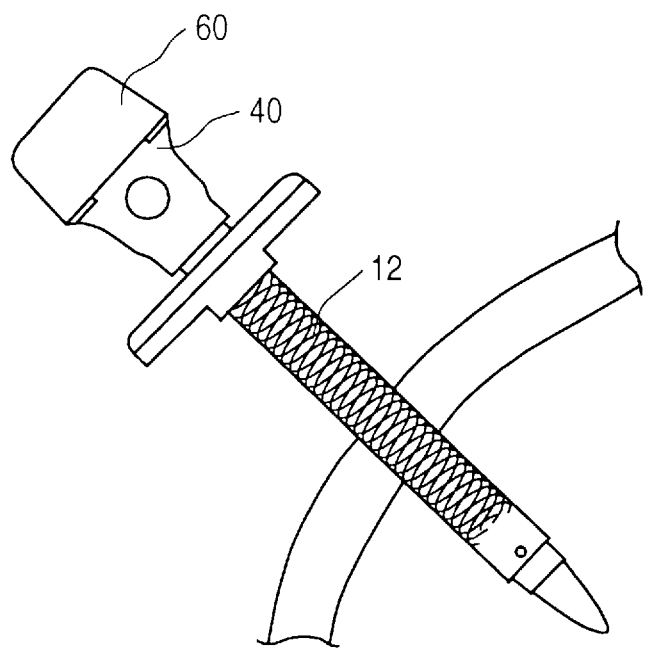
Figure 21:
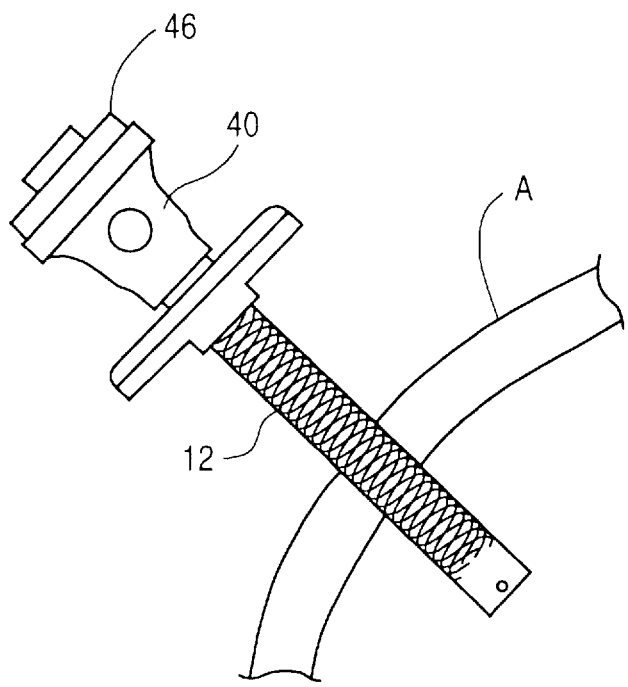

Referring now to FIGS. 18–21, use of the access system of the present invention will be described in detail. Initially, a radially expandable sleeve 10 having a pneumoperitoneum needle 20 inserted therein is introduced through patient's abdomen A (or other body location) by engaging the sharpened distal end 36 of the needle against the tissue and advancing the assembly until the body 12 of the sleeve extends across the tissue. The pneumoperitoneum needle 20 is then removed, and an expansion assembly comprising the cannula 40 and obturator 60 is introduced through the sleeve 10, resulting in radial expansion of the sleeve body 12, as illustrated in FIG. 20. The obturator 60 is then removed, leaving an access channel through the abdominal wall A, as illustrated in FIG. 21.

After use of the system, the valve cap 46 and radially expandable sleeve 10 will usually be discarded. Because of the expanded or spent configuration of the sleeve, the sleeve cannot be reused. The valve cap will usually be discarded since cleaning of the internal components is difficult and the cost of a disposable valve cap is relatively low. The remaining components of the system, however, can be reused after appropriate cleaning and sterilization. As set forth in Table 1 above, the tubular needle body and cannula tube are available for a limited reuse, but will typically wear sufficiently after from 5–30 additional uses, that they should be discarded. The needle stylet, cannula hub, and obturator, however, may be reused a relatively unlimited number of times, usually more than 100, before needing replacement. The components, however, are of course subject to wear and tear and breakage, at which times these system components will also have to be replaced.

Although the foregoing invention has been described in some detail by way of illustration and example, for purposes of clarity of understanding, it will be obvious that certain changes and modifications may be practiced within the scope of the appended claims.

What is claimed is:

1. A method for reusing an access system, wherein the access system comprises the following components each of which have been previously used to access a target location in a patient:

a radially expandable sleeve having an axial lumen therethrough;

a cannula including a cannula tube having a proximal end, a distal end, and a lumen therethrough, and a cannula hub attached to the proximal end of the cannula tube and having a removable valve cap thereon; and an obturator removably receivable in the lumen of the cannula tube, said obturator having a tapered distal end which extends distally from the distal end of the cannula body when the obturator is therein;

wherein the method comprises the steps of:

replacing at least the radially expandable sleeve and the valve cap; and sterilizing at least one of the other system components and sterilizing or replacing all other components of the system.

2. A method as in claim 1, wherein the cannula tube is removably attached to the cannula hub, further comprising the steps of separating the tube and hub, cleaning and sterilizing the cannula hub, and replacing the cannula tube.

3. A method as in claim 1, wherein the access system further comprises a needle component including a tubular needle and a stylet removably received in the needle, further comprising the step of cleaning and sterilizing the stylet and replacing the needle.

4. A method as in claim 1, wherein the cannula tube and hub and the obturator are cleaned and sterilized, further comprising reconstructing an expansion assembly by attaching the replacement valve cap on the cleaned and sterilized cannula tube and hub and inserting the cleaned and sterilized obturator through the cannula tube and hub.

5. A method as in claim 1, wherein the cannula tube is replaced and the cannula hub and obturator are cleaned and sterilized, further comprising reconstructing an expansion assembly by attaching the replacement valve cap on the sterilized cannula hub, attaching the replacement cannula tube to the cannula hub, and inserting the sterilized obturator through the cannula tube and hub.

6. A method as in claim 1, wherein the access system further comprises a needle component including a tubular needle and a stylet removably received in the needle, further comprising reconstructing an expansion assembly by inserting the needle component in a central lumen of the replaced radially expandable sleeve.

7. A method as in claim 6, further comprising cleaning and sterilizing both the needle and the stylet, and inserting the stylet through the needle before inserting the needle component in the radially expandable sleeve.

8. A method as in claim 6, further comprising replacing at least the needle, and inserting the stylet through the needle before inserting the needle component in the radially expandable sleeve.

9. A method as in claim 6, further comprising replacing both the needle and the stylet, and inserting the stylet through the needle before inserting the needle component in the radially expandable sleeve.

10. A kit for use in reconstructing an access system, wherein the access system comprises the following components:

a radially expandable sleeve having an axial lumen therethrough;

a cannula including a cannula tube having a proximal end, a distal end, and a lumen therethrough, and a cannula hub attached to the proximal end of the cannula tube and having a removable valve cap thereon; and an obturator removably receivable in the lumen of the cannula tube, said obturator having a tapered distal end which extends distally from the distal end of the cannula body when the obturator is therein;

wherein the kit comprises:
- a radially expandable sleeve and a valve cap; and
- a package enclosing the radially expandable sleeve and the valve cap.

11. A kit for use in reconstructing an access system, wherein the access system comprises the following components:
- a radially expandable sleeve having an axial lumen therethrough;
- a cannula including a cannula tube having a proximal end, a distal end, and a lumen therethrough, and a cannula hub attached to the proximal end of the cannula tube and having a removable valve cap thereon; and
- an obturator removably receivable in the lumen of the cannula tube, said obturator having a tapered distal end which extends distally from the distal end of the cannula body when the obturator is therein;

wherein the kit comprises:
- a valve cap; and
- a sterile package enclosing the valve cap.

12. A kit for use in reconstructing an access system as in claim 11, wherein the kit further comprises:
- a cannula tube and hub; and
- wherein the package also encloses the cannula tube and hub.

13. A kit as in claim 12, further comprising an obturator disposed in the package.

14. A kit for use in reconstructing an access system as in claim 11, wherein the kit further comprises:
- a cannula body; and
- wherein the package also encloses the cannula body.

15. A kit as in claim 14, further comprising a stylet disposed in the package.

16. A kit for use in reconstructing an access system as in claim 11, wherein the kit further comprises:
- a tubular needle; and
- wherein the package encloses the tubular needle.

17. An access system comprising:
- a radially expandable sleeve having an axial lumen therethrough;
- a cannula assembly including a cannula tube having a proximal end, a distal end, and a lumen therethrough, and a cannula hub removably attachable to the proximal end of the cannula tube;
- a valve cap having a pneumostasis valve therein, said valve cap removably attachable to the cannula hub; and
- an obturator removably receivable in the lumen of the cannula tube, said obturator having a tapered distal end which extends distally from the distal end of the cannula body when the obturator is therein.

18. An access system as in claim 17, further comprising a pneumoperitoneum needle.

19. An access system as in claim 17, wherein the pneumoperitoneum needle comprises a tubular needle and an internal stylet removably received in the tubular needle.

* * * * *